United States Patent
Mashouf (10) Patent No.: US 10,433,933 B2
(45) Date of Patent: Oct. 8, 2019

(54) ORTHODONTIC BRACKET FOR USE ON DECIDUOUS TEETH

(76) Inventor: Cameron Mashouf, San Jose, CA (US)

(*) Notice: Subject to any disclaimer, the term of this patent is extended or adjusted under 35 U.S.C. 154(b) by 0 days.

(21) Appl. No.: 13/050,385

(22) Filed: Mar. 17, 2011

(65) Prior Publication Data

US 2012/0237887 A1    Sep. 20, 2012

(51) Int. Cl.
*A61C 7/02* (2006.01)
*A61C 7/14* (2006.01)
*A61C 7/16* (2006.01)

(52) U.S. Cl.
CPC .............. *A61C 7/023* (2013.01); *A61C 7/14* (2013.01); *A61C 7/16* (2013.01)

(58) Field of Classification Search
CPC .............. A61C 7/023; A61C 7/14; A61C 7/16
USPC .................................................. 433/8–17, 24
See application file for complete search history.

(56) References Cited

U.S. PATENT DOCUMENTS

| | | | |
|---|---|---|---|
| 4,830,612 A | 5/1989 | Bergersen | |
| 4,871,310 A * | 10/1989 | Vardimon | A61C 7/006 433/18 |
| 5,035,612 A | 7/1991 | Martin | |
| 5,062,793 A | 11/1991 | Cleary | |
| 5,098,288 A | 3/1992 | Kesling | |
| 5,158,452 A * | 10/1992 | Franseen | A61C 7/12 433/24 |
| 5,226,814 A * | 7/1993 | Allen | A61C 7/12 433/15 |
| 5,263,859 A | 11/1993 | Kesling | |
| 5,362,232 A | 11/1994 | Franseen | |
| 5,395,237 A * | 3/1995 | Pospisil | A61C 7/14 29/896.11 |
| 5,645,421 A | 7/1997 | Slootsky | |
| 6,280,184 B1 | 8/2001 | Hamilton | |
| 6,474,988 B1 | 11/2002 | Georgakis | |
| 7,252,505 B2 * | 8/2007 | Lai | A61C 7/30 433/11 |
| 7,452,205 B2 | 11/2008 | Cinander, Jr. | |
| 7,549,860 B2 | 6/2009 | Soo | |
| 7,581,949 B2 | 9/2009 | Farzin-Nia | |
| 7,670,140 B2 | 3/2010 | Hart | |

(Continued)

FOREIGN PATENT DOCUMENTS

WO    WO-2011087985 A1 *    7/2011

*Primary Examiner* — Heidi M Eide
*Assistant Examiner* — Mirayda A Aponte
(74) *Attorney, Agent, or Firm* — Kilpatrick Townsend & Stockton LLP (57) ABSTRACT

The present invention relates to an orthodontic bracket specifically designed for use with the deciduous teeth and method for its use. The bracket is unique in providing a debonding tab which reduces the potential for damage to the tooth due to the application of excessive force during the debonding process. The small size of the bracket allows it to fit available crown space on the deciduous teeth. Further the bracket is modified in shape to minimize mechanical forces applied to the deciduous teeth when engaged with an archwire. The bracket base is shaped to conform to the morphology of the deciduous tooth crown surface thereby providing an optimal adhesive interface with the deciduous tooth. The deciduous bracket provides adequate adhesion to avoid unwanted detachment of the bracket which often occurs when the use of permanent brackets is attempted on the deciduous teeth.

6 Claims, 10 Drawing Sheets

(56) References Cited

U.S. PATENT DOCUMENTS

| | | |
|---|---|---|
| 7,819,660 B2 | 10/2010 | Cosse |
| 2004/0219470 A1 | 11/2004 | Farzn-Nia |
| 2005/0136370 A1 | 6/2005 | Brennan |
| 2006/0019211 A1 | 1/2006 | Ricketts |
| 2006/0127835 A1 | 6/2006 | Soo |
| 2006/0275729 A1 | 12/2006 | Fornoff |
| 2007/0207435 A1* | 9/2007 | Devanathan ............ 433/9 |
| 2008/0138757 A1* | 6/2008 | Lai et al. ............ 433/10 |
| 2008/0153051 A1 | 6/2008 | Hart |
| 2009/0305183 A1* | 12/2009 | Chen ............ 433/8 |
| 2011/0081622 A1* | 4/2011 | Mashouf ............ 433/10 |

* cited by examiner

ORTHODONTIC BRACKET FOR USE ON DECIDUOUS TEETH

FIELD OF THE INVENTION

This invention relates to the use of orthodontic brackets on deciduous teeth to correct tooth alignment.

BACKGROUND OF THE INVENTION

One type of common orthodontic treatment involves the use of a set of tiny appliances commonly known as brackets and buccal tubes. Buccal tubes are normally mounted on the molars and brackets are attached to all other teeth. Each bracket is secured to a corresponding tooth through a bonding adhesive which is sandwiched between the pad of bracket on one side and enamel surface of the tooth on the other side. Each bracket has a slot to receive a resilient archwire. The slot forms a track to guide movement of the teeth to desired positions. Ends of archwire are commonly placed in slots or channels of buccal tube appliances that are attached to the molar teeth either through bonding with adhesive or first welded on a band and then cemented on the tooth.

Use of Brackets on Deciduous Teeth

Up to the present time, the orthodontic brackets and tubes (braces) which are available in the market have been designed for permanent teeth. Several forms of bite problems (malocclusion) develop during childhood in the deciduous (primary) dentition. Most common amongst them are cross bites of the anterior or posterior teeth. The advances in our understanding of children growth and development and in interceptive orthodontics have made the treatment of younger children more desirable.

Such treatment is done during the deciduous (primary) dentition or during mixed-dentition period when the deciduous teeth are still present. There are circumstances that early correction of a malocclusion during deciduous or mixed-dentition periods would either prevent or reduce the extent of treatment at a later date.

Deciduous teeth can be moved to allow better jaw relationship, to make room for the permanent teeth or used as anchors for more efficient movement of the permanent teeth. Malocclusions that involve deciduous teeth are simpler and easier to correct that malocclusion of permanent teeth. This is due to the younger age of the patients for whom the tissues surrounding deciduous teeth are more adaptive and allow faster movement of the deciduous teeth with smaller increments of force.

Due to a lack of availability of brackets and tubes for the deciduous teeth, the orthodontists are forced to either defer the treatment to allow the development of permanent dentition or use the appliances that are designed for permanent teeth and place them on the deciduous teeth. Due to different size and shape of these teeth the permanent teeth bracket bases do not adapt well to the deciduous teeth surfaces. Further, studies performed in Japan (American Journal of Orthodontics and Dentofacial Orthopedics Vol. 134/2008 pp. 198-208 article—"Comparison of shear bond strengths of orthodontic brackets bonded to deciduous and permanent teeth" by Endo, T. et. al.) have shown that permanent brackets bond more weakly to deciduous as opposed to permanent teeth. The researchers attributed the weak bonding to a difference in the chemical structure of the enamel found on deciduous teeth as compared to permanent teeth. As a result of these and other factors, brackets bonded to deciduous teeth frequently come loose during the course of treatment creating inconvenience and frustration for both the patient and the dentist.

Additionally, the mode and rate of movement of deciduous teeth is different from permanent teeth. The brackets that are designed for permanent teeth are too large for the deciduous teeth therefore interfere with proper brushing, cause impingement of the gum tissues and apply several unnecessary force vectors on the deciduous teeth.

Debonding

Debonding brackets from deciduous teeth may also be a problem. Deciduous teeth become progressively looser prior to falling out due to the resorption of their roots. Therefore they may not have the structural integrity to easily sustain the pressure required for removal of a bracket as would a permanent tooth.

Metal brackets are commonly debonded using a plier-type hand instrument. Force is typically applied in the mesial-distal or diagonal direction causing deformation in the ductile bracket body. This deformation effects a separation or fracture at the interface between the bonding adhesive and the bracket base allowing the bracket to be peeled or pried away from the tooth surface.

DESCRIPTION OF RELATED ART

Brackets made of materials more brittle than metal, such as ceramic, are not easily peeled or pried away from the tooth surface and tend to fracture under an applied force. An attempt to apply mesial-distal force as described with metal brackets generally results in the fracture of the tie wings or other portions of the bracket. Various tools have been put forward to remedy this problem (e.g. U.S. Pat. No. 4,950,157 to Cleary, U.S. Pat. No. 4,904,183 to Hannan and U.S. Pat. No. 6,382,965 to Ruiz-Vela), but none has provided a complete solution.

U.S. Pat. No. 5,439,379 to Hansen discloses an orthodontic bracket design, the purpose of which is to facilitate the debonding of ceramic orthodontic brackets. The disclosed design provides for a bracket with mesial and distal sections separated by an elongated channel extending generally in the occlusal-gingival direction. During debonding the pressure applied with a tool such as pliers causes the mesial and distal sections to pivot towards each other, thereby applying pressure to the bonding surfaces. In theory this design puts significantly less stress on the bracket in order to effectuate debonding than would be the case with a conventional ceramic orthodontic bracket.

BRIEF SUMMARY OF THE INVENTION

The present invention relates to an orthodontic bracket specifically designed for use with the deciduous teeth and method for its use. The deciduous teeth have been shown by various practitioners to be particularly useful anchors for the alignment of permanent teeth when integrated into a dental appliance. The bracket is unique in providing a debonding tab which reduces the potential for damage to the tooth due to the application of excessive force during the debonding process. The small size of the bracket allows it to fit available crown space on the deciduous teeth. Further the bracket is modified in shape to minimize mechanical forces applied to the deciduous teeth when engaged with an archwire. The bracket base is shaped to conform to the morphology of the deciduous crown surface thereby providing an optimal adhesive interface with the deciduous tooth. The deciduous bracket provides adequate adhesion to avoid unwanted detachment of the bracket which often occurs when the use of permanent brackets is attempted on the deciduous teeth.

DETAILED DESCRIPTION OF THE INVENTION

The following description is presented to enable any person skilled in the art to make and use the disclosed embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present description. Thus, the present description is not intended to be limited to the embodiments shown, but is to be accorded the widest scope consistent with the principles and features disclosed herein.

For the purposes of this disclosure the term "deciduous bracket" refers to an orthodontic bracket particularly designed for use on a deciduous human tooth.

Orthodontic treatment is defined as correction of misaligned teeth and improper bite. Alignment of crooked teeth and correction of bite problems are accomplished by devices that are referred to as orthodontic appliances. The most common type of orthodontic appliances are called fixed appliances or braces. Fixed appliances include tiny pieces called brackets which are secured to the teeth and serve as handles to move the teeth. Brackets have a slot to receive an arch wire. Bracket slots form a track to guide movement of the teeth to desired positions. Ends of the archwire are commonly placed in channels called buccal tubes which are mounted on the patient's molar teeth. Brackets and buccal tubes are collectively called attachments.

A large proportion of orthodontic treatment is done around adolescence which corresponds with completion of the so called permanent dentition. For this reason, the orthodontic attachments are designed to optimally fit the permanent teeth. However, misalignment of teeth and improper bite (malocclusion) usually become noticeable in early mixed-dentition at the age of about seven. In this stage of a child's development, the permanent first molars erupt in the posterior region of the mouth and the permanent incisors erupt in the anterior region. Deciduous canines, first and second molars which are interposed between the permanent first molars and incisors continue their presence and function for at least four more years in the buccal segments, hence the term mixed dentition.

For many forms of malocclusion the mixed-dentition period provides an optimal treatment time. The treatment that commences during mixed-dentition is called interceptive orthodontic treatment. There are rare circumstances that treatment is indicated prior to mixed dentition period, in children younger than seven years of age, during the so called deciduous dentition. Treatment that is initiated in mixed-dentition has to consider the presence of the deciduous teeth which occupy a significant portion of the dental arches. At the present time a practitioner who engages in interceptive orthodontic treatment, has two choices:

1. Placement of the attachments on the permanent teeth and bypassing the deciduous teeth in the dental arch. The appliance design used in this technique is commonly called the 2 by 4 appliance. Generally speaking, the 2 by 4 approach is inefficient due to the long, unsupported spans of arch wires that connect the permanent molars to permanent incisors.

2. Inclusion of the deciduous teeth in the appliances by using the brackets of permanent teeth and placing them on the deciduous teeth as well as the permanent teeth. In this approach the brackets do not adapt well to the deciduous teeth and detach frequently causing delays and discomfort for the practitioner and patient.

The present invention involves a new design brackets specifically for attachment to the deciduous teeth. A major feature of the deciduous brackets is the bracket base which is adapted to the surface morphology of the deciduous molars and canines.

Advantages of Using Deciduous Teeth in Interceptive Treatment

Deciduous teeth can be used as anchors to move the permanent teeth more efficiently. They can also be moved to allow more space for the permanent teeth. Using brackets on the deciduous teeth and their inclusion in the mechanics of tooth movement increases the efficiency of the appliances in the following circumstances:

1. Correction of crowding: Development of additional space and the supportive structures for permanent teeth is accomplished through expansion of the posterior segments. In the maxillary arch a rapid palatal expansion appliance is used to expand the maxilla using the permanent and deciduous teeth in the posterior segments as anchors. Once there is adequate space, the deciduous teeth and permanent incisors are bracketed. A series of arch wires are used for leveling and alignment of the incisors using deciduous canines as anchors for alignment of the incisors. Due to proximity of the deciduous canines to the permanent incisors, they serve as ideal anchor teeth for efficient alignment of the incisors. In the mandibular arch a removable lingual arch is employed initially to expand the permanent first molars. The deciduous canines and molars are bonded along with the permanent incisors once adequate expansion of the permanent molars is achieved. The deciduous molars and canines are expanded and incisors are leveled and aligned with a series of arch wires using permanent molars as anchors.

2. Correction of deep bite and open bite cases: Intrusion and extrusion of the permanent incisors are facilitated by using the deciduous teeth as anchors. In the maxillary arch the deciduous canine brackets are angled either upward or downward to apply the corresponding bite opening or closing forces to the maxillary incisors. In the mandibular arch opening of bite is facilitated by progressively positioning the deciduous brackets more gingival and by tilting them so that their mesial aspects point downward from the second deciduous molar to deciduous canine.

3. Correction of cross bites: There are many different types of cross bite which require different approaches to their treatment plan. Deciduous brackets can offer more efficient means of correcting various types of cross bites. For correction of a complex cross bite involving both upper and lower dental arches, expansion of maxilla and mandibular arch are accomplished with a maxillary expansion appliance (MEA) and a lower lingual arch (LLA) respectively. Maxillary incisors are advanced using stops in the arch wires. Mandibular incisors are retracted using the additional space provided by expansion of the permanent and deciduous molars and canines. In the correction of skeletal cross bites due to a maxillary under development, a face mask or reverse pull head gear can be employed. Intermaxillary elastics can also be also be used for additional effects. In the cases of simpler forms of cross bites such as those involving one arch or only a portion of the dental arch, the mechanics should be simplified to reflect the less complex nature of these cases.

Figure 1:
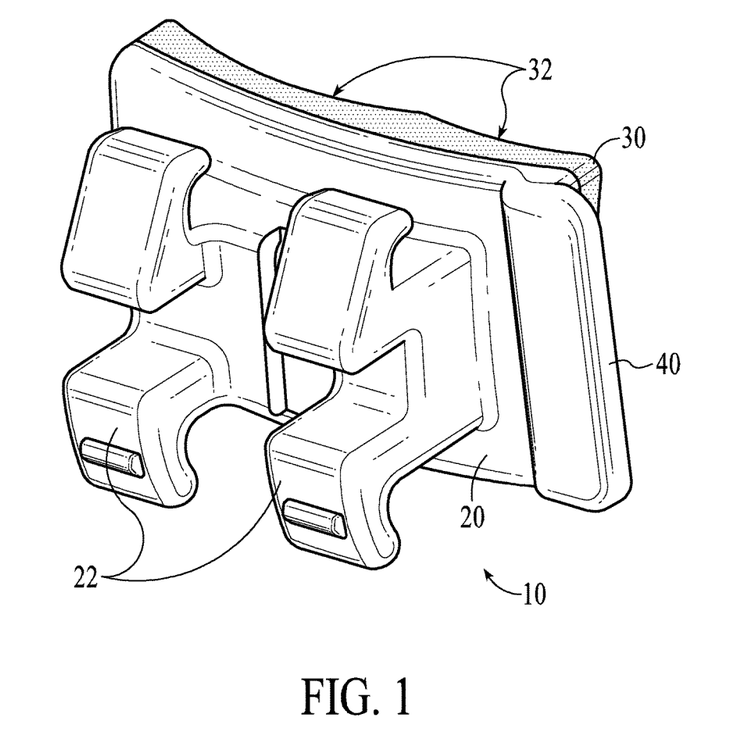
FIG. 1 is a perspective view of an embodiment of a deciduous bracket.

4. Correction of impacted permanent first molars: Occasionally, the permanent first molars develop ectopically under the distal bulge of the deciduous second molars. The affected permanent molar can be corrected through sectional mechanics with bonded brackets on the adjacent deciduous molars and the impacted first molar. The present invention provides the practitioners with simple and inexpensive attachments for the deciduous teeth. The anatomically designed bases of these attachments allow adequate adaptation to the surface of the deciduous teeth and therefore bond reliably to the enamel of the deciduous teeth. Inclusion of the deciduous teeth in the mechanics of tooth movement increases the efficiency of the appliances and provides new and innovative approaches for the treatment of children during mixed-dentition FIG. 1 shows a perspective view of an embodiment of a deciduous bracket 10. In this embodiment bracket base 30 conforms to a deciduous tooth crown surface by means of two base indentations 32. This arrangement of indentations is particularly well adapted for use on a deciduous first molar. Debonding tab 40 is a horizontal extension of the buccal body surface 20 situated in this embodiment on the mesial side of deciduous bracket 10. Tie wings 22 allow for the engagement of an archwire.

Figure 2:
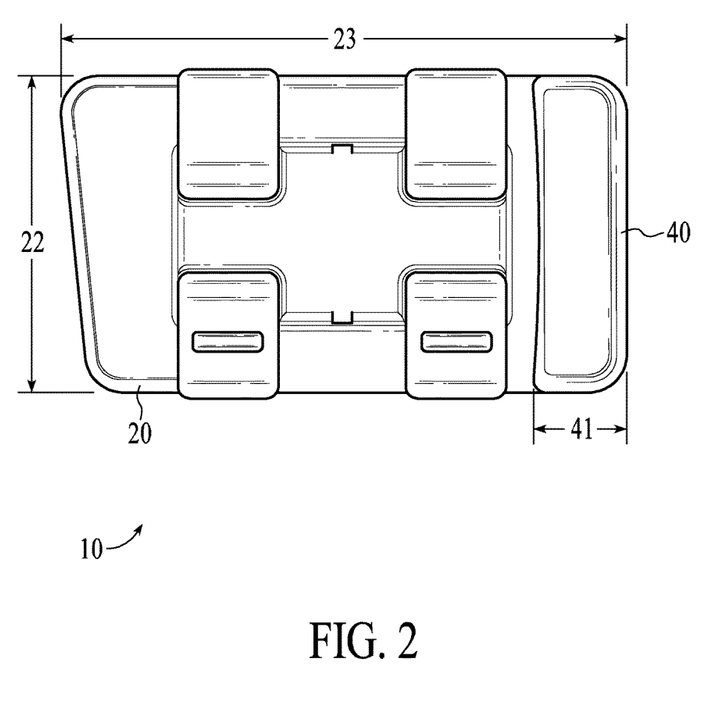
FIG. 2 is a buccal view of a deciduous bracket.

FIG. 2 is a buccal view of deciduous bracket 10. The occlusal-gingival dimension 22 and mesio-distal 23 dimension of deciduous bracket 10 are both uniquely sized to provide maximum surface area contact between deciduous bracket 10 and a deciduous tooth. Maximizing the bracket surface area in contact with the deciduous tooth crown surface is an important factor in maintaining a solid bond between a deciduous bracket and the crown surface of a deciduous tooth. The debonding tab width 41 of debonding tab 40 determines the size of the access area available for interaction with a debonding tool, as further explained below.

Figure 3:
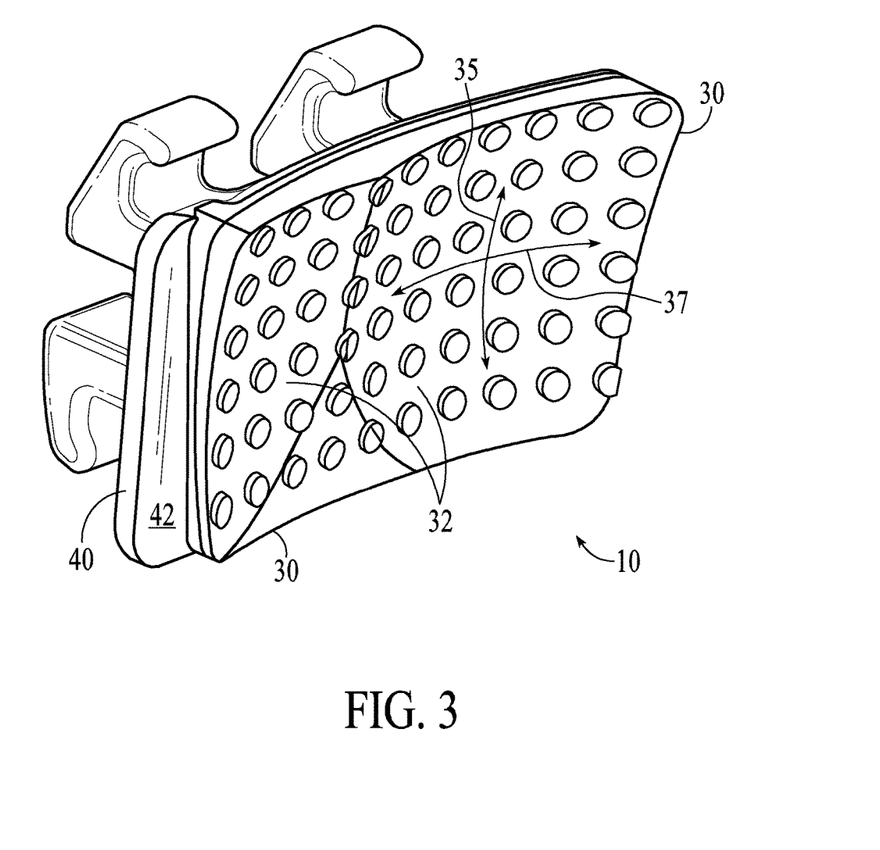
FIG. 3 is a second perspective view of a deciduous brackets showing base indentations.

FIG. 3 is a second perspective view of an embodiment of deciduous bracket 10. Two indentations 32 of bracket base 30 are shown. Directional arrow 37 describes the mesio-distal radius of a base indentation 32. The mesio-distal radius of a base indentation 32 can range from about 3 to about 4.5 mm. The radius in the occlusal-gingival plane is represented by directional arrow 35 and can range from about 4.5 to about 6.5 mm. Curvature of the bracket base indentations corresponding to these radii provide for optimal bonding between a bracket surface and the corresponding deciduous tooth crown surface. Also shown in FIG. 3 is debonding tab 40 and the debonding tab lingual surface 42. It can be seen here that debonding tab lingual surface 42 is recessed buccally as compared to the bracket base 30, thereby forming debonding access area 80 (FIG. 8) beneath the debonding tab.

Figure 4:
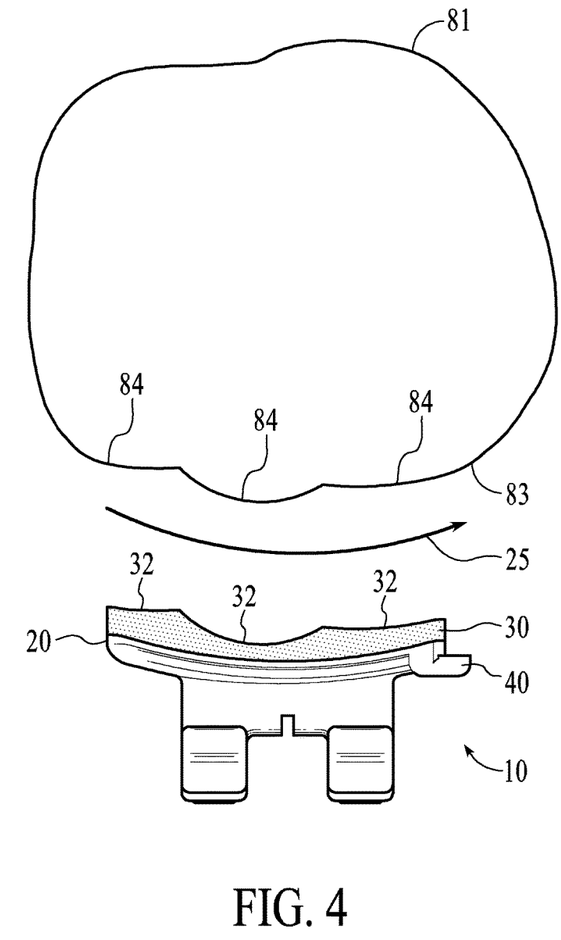
FIG. 4 is an occlusal view of a deciduous bracket designed for use on a deciduous lower second molar.

FIG. 4 shows an occlusal view of an embodiment of deciduous bracket 10 designed specifically for use on a lower deciduous second molar 81. It can be seen that the base indentations 32 correspond to cusps 84 of the deciduous lower second molar 81 to facilitate tight bonding using a minimal amount of adhesive. Directional arrow 25 describes the overall radius of bracket base 30. The radius for this embodiment can range from about 8 to 11 mm. and corresponds to the overall curvature of the buccal crown surface 83 of deciduous second molar 81. In this embodiment debonding tab 40 extends mesially from the buccal body surface 20 of deciduous bracket 10.

Figure 5:
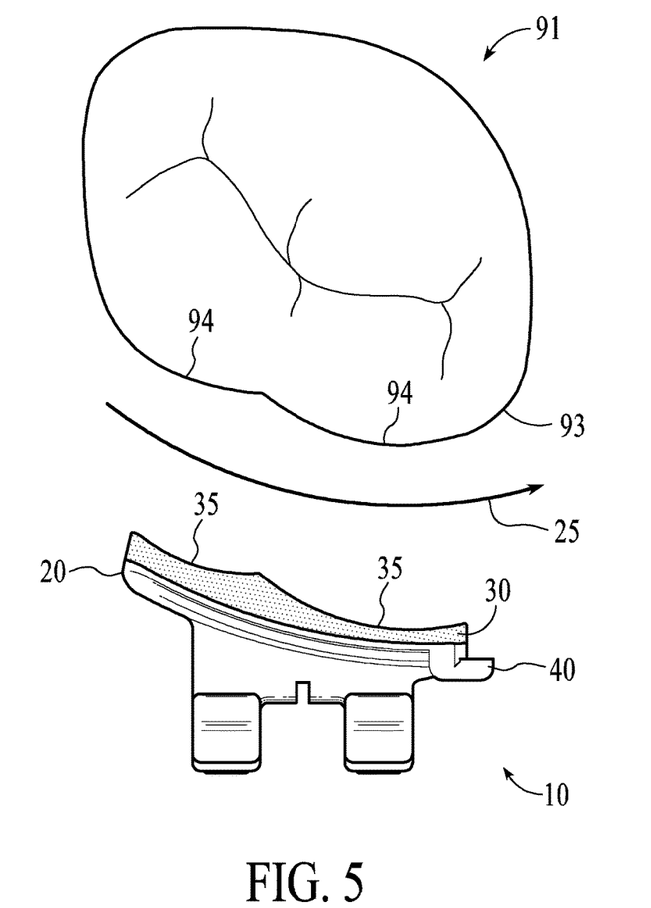
FIG. 5 is an occlusal view of a deciduous bracket designed for use on a deciduous lower first molar or upper deciduous first molar or upper deciduous second molar.

FIG. 5 shows an occlusal view of an embodiment of deciduous bracket 10 designed for use on a lower deciduous first molar 91. This particular embodiment can also be used on an upper deciduous first molar (not shown) or upper deciduous second molar (not shown). Again it can be seen that the base indentations 32 correspond to cusps 94 of the deciduous lower first molar 91 to facilitate tight bonding. Directional arrow 25 describes the overall radius of bracket base 30. This radius for this embodiment can range from about 3 to about 11 mm. and corresponds to the overall curvature of the buccal crown surface 93 of deciduous first molar 91.

Figure 6:
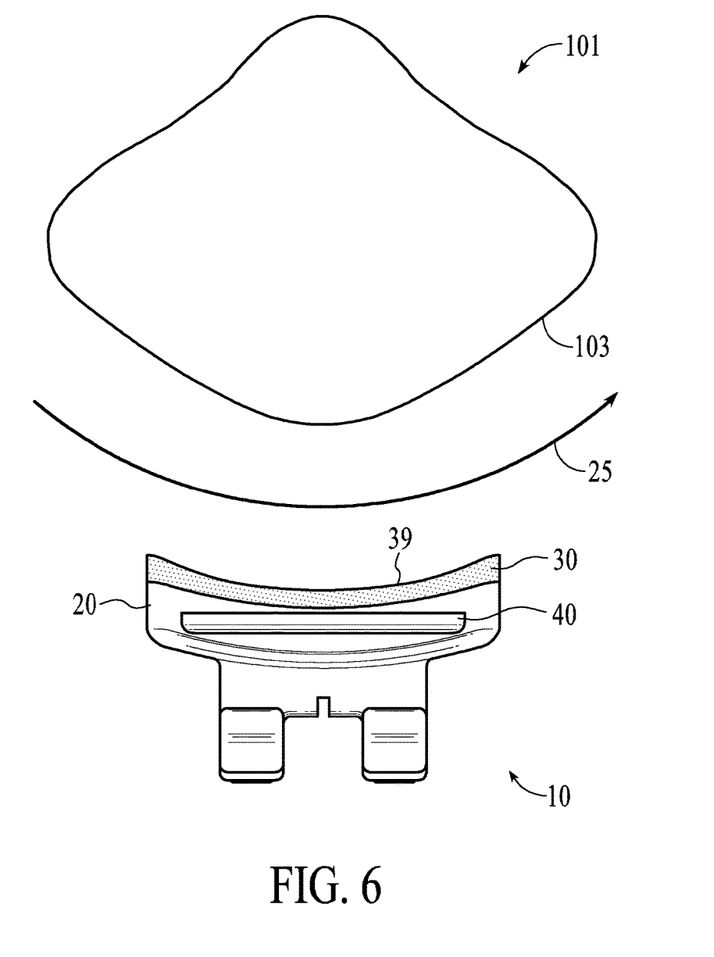
FIG. 6 is an occlusal view of a deciduous bracket designed for use on a deciduous canine tooth.

FIG. 6 is an occlusal view of an embodiment of deciduous bracket 10 for use a deciduous canine tooth 101. In this embodiment the base surface 39 is smoothly curved to conform to occlusal surface 103 of deciduous canine tooth 101. Radius arrow 25 describes the overall radius of bracket base 30. The radius for this embodiment can range from about 2 to 4.5 mm. Debonding tab 40 extends occlusally from buccal body surface 20 of deciduous bracket 10.

Figure 7:
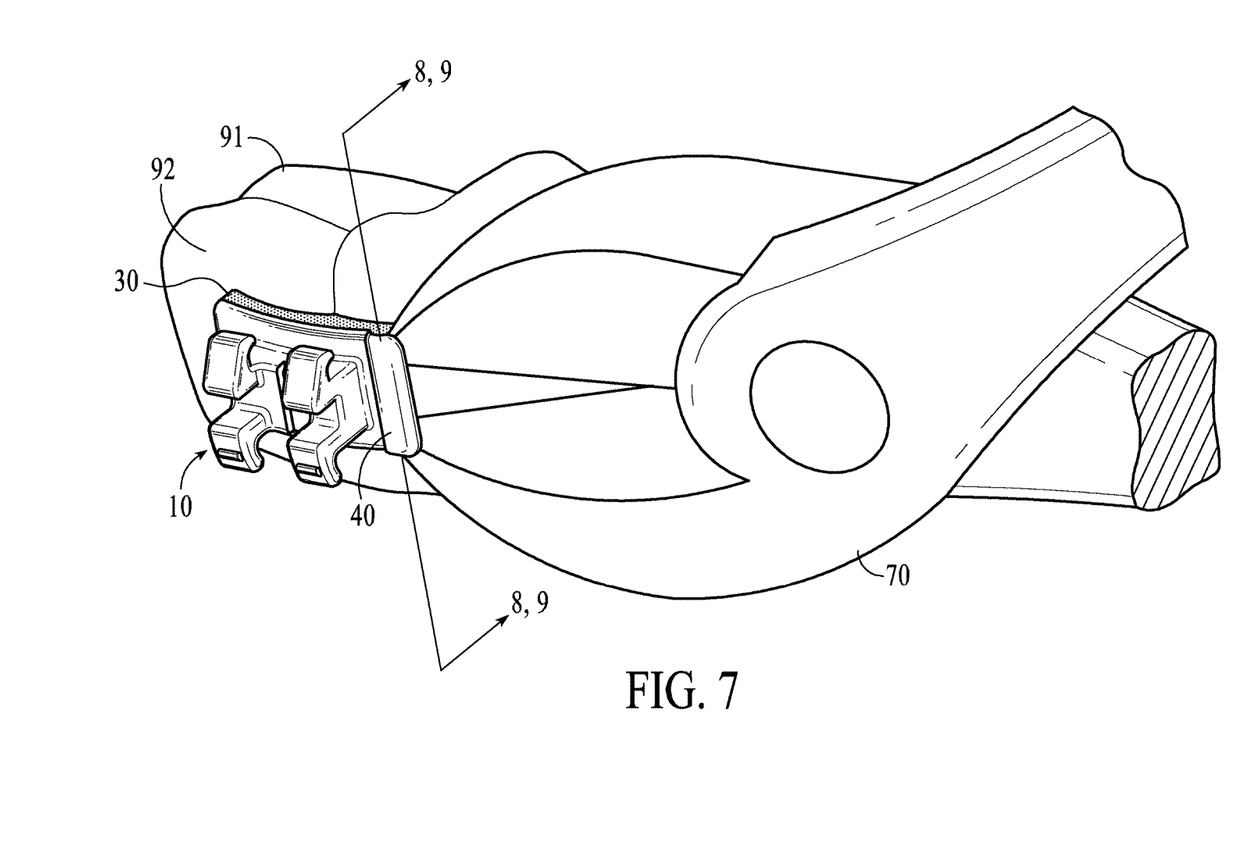
FIG. 7 depicts the process of debonding a deciduous bracket from a deciduous tooth prior to introduction of the debonding tool.
Figure 8:
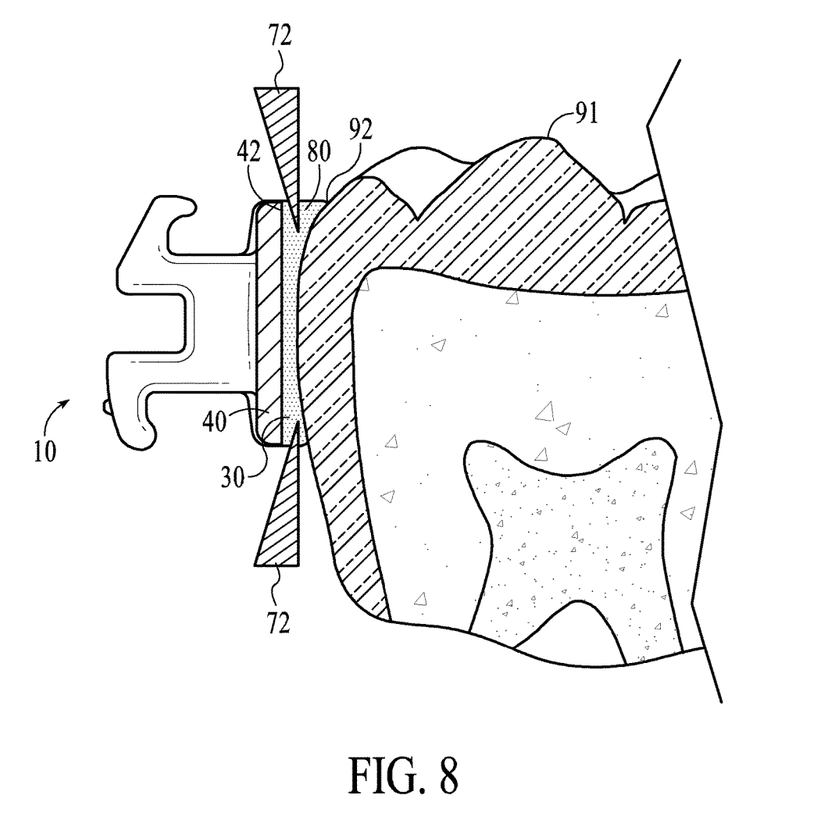
FIG. 8 depicts the process of debonding a deciduous bracket from a deciduous tooth with the debonding tool in an intermediate position.
Figure 9:
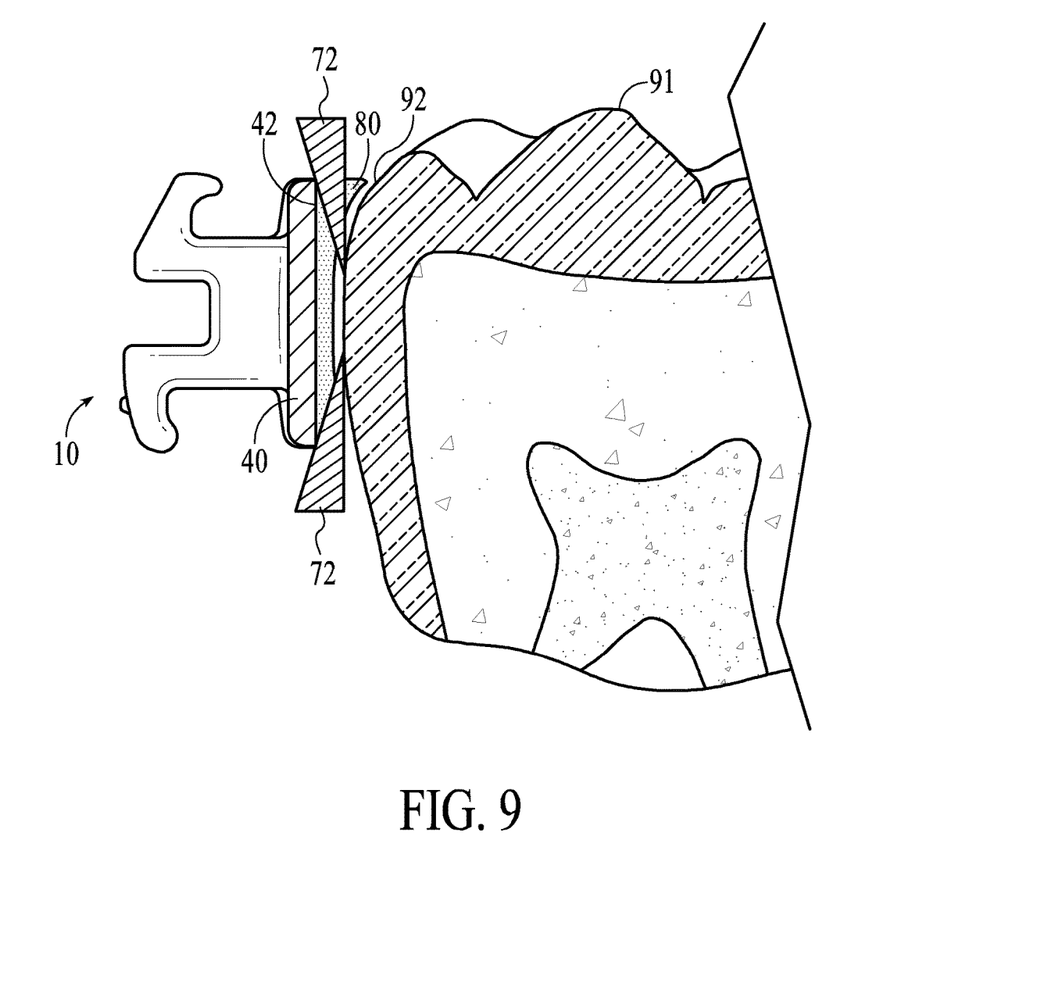
FIG. 9 depicts the process of debonding a deciduous bracket from a deciduous tooth where debonding has been completed.

FIG. 7-FIG. 9 depicts the debonding process as it would occur on any deciduous tooth. The lingual surface of the debonding tab provides a convenient access area for a debonding tool allowing removal of the bracket from a tooth while exerting minimal pressure on the tooth. This is important since deciduous teeth become progressively looser as a child ages and the pressure required for bracket removal can be quite uncomfortable for the child. FIG. 7 is a perspective view of deciduous bracket 10 attached to the buccal crown surface 92 of a deciduous first molar 91. The tips 72 (shown in FIG. 8) of debonding tool 70 are inserted beneath debonding tab 40 as an initial step in the debonding process. FIG. 8 is a cross sectional view of deciduous bracket 10 as seen along reference line 8,9 of FIG. 7 Again we see deciduous bracket 10 attached to the buccal crown surface 92 of deciduous first molar 91 during the initiation of the debonding process. Tips 72 of debonding tool 70 have been introduced into debonding access area 80 but are not yet in contact with lingual surface 42 of debonding tab 40. FIG. 9 shows the same cross sectional view and features as FIG. 8, as seen along reference line 8,9 of FIG. 7. Here, the tips 72 of debonding tool 70 have been further inserted into debonding access area 80 and are in contact with both the lingual surface 42 of debonding tab 40 and the buccal crown surface 92 of deciduous first molar 91. The simultaneous forces applied by the debonding tool against crown surface 92 and debonding tab 40 effectuate debonding of deciduous bracket 10 from deciduous first molar 91.

Figure 10:
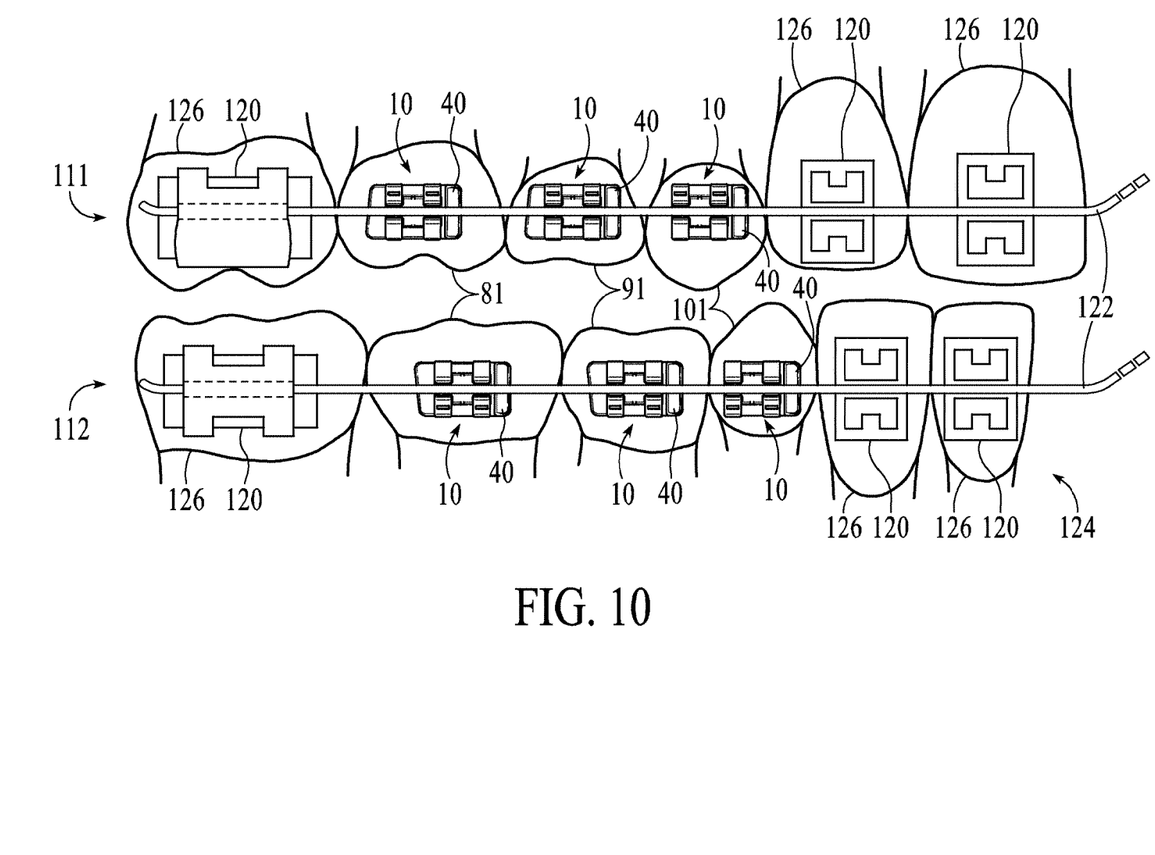
FIG. 10 is a side view of a dental appliance on mixed dentition and having both deciduous brackets and permanent orthodontic brackets.

FIG. 10 depicts one possible method of using deciduous brackets for the correction of misaligned teeth and bite problems on upper and lower mixed dentition dental arches. Dental appliance 124 is shown on upper and lower dental arches, 111 and 112 respectively. Dental appliance 124 is comprised of deciduous brackets 10 on second deciduous molars 81, first deciduous molars 91 and deciduous canines 101. Dental appliance 124 is further comprised of permanent brackets 120 attached to permanent teeth 126, and archwires 122.

The foregoing descriptions of embodiments have been presented for purposes of illustration and description only. They are not intended to be exhaustive or to limit the present invention to the forms disclosed.

Accordingly, many modifications and variations will be apparent to practitioners skilled in the art. Additionally, the above disclosure is not intended to limit the present invention. The scope of the present invention is defined by the appended claims.

I claim:

1. A method of correcting tooth misalignment in mixed dentition, the method comprising:
    attaching a deciduous bracket to a buccal crown surface of a deciduous tooth as a component of a dental appliance, which is also comprised of orthodontic brackets attached to one or more permanent teeth, wherein the attached deciduous bracket comprises:
        a base attached to the buccal crown surface of the deciduous tooth;
        a body comprising a first buccal surface facing away from the buccal crown surface of the deciduous tooth and one or more tie wings for the attachment of an archwire; and
        a debonding tab extending horizontally away from the first buccal surface of the body with the base attached to the buccal crown surface of the deciduous tooth and extending in an occlusalgingival direction along a mesial side of the body, wherein the debonding tab comprises a lingual surface facing and spaced in a buccolingual direction from the buccal crown surface of the deciduous tooth with the base attached to the buccal crown surface of the deciduous tooth, and wherein the debonding tab defines a recess between the buccal crown surface of the deciduous tooth and the lingual surface accessible by a debonding tool;
    employing a series of arch wires used for leveling and alignment of the permanent teeth while using the deciduous tooth as an anchor; and
    removing the deciduous bracket from the deciduous tooth using the debonding tool by inserting the debonding tool between the lingual surface of the debonding tab and the buccal crown surface of the deciduous tooth and applying simultaneous force against the lingual surface of the debonding tab and the buccal crown surface of the deciduous tooth with the debonding tool from only the mesial side of the body in order to remove the deciduous bracket from the deciduous tooth.

2. The method of claim 1, wherein an occlusalgingival dimension of the base is in the range of 2 mm to 3 mm.

3. The method of claim 2, wherein a mesiodistal dimension of the base is in the range of 3 mm to 5 mm.

4. The method of claim 3, wherein the base defines one or more semispherical indentations configured for bonding to a cusp of the deciduous tooth; wherein each indentation comprises a mesiodistal radius of curvature of 3-4.5 mm and an occlusalgingival radius of curvature measuring 4.5-6.5 mm.

5. The method of claim 4, wherein the deciduous tooth is an upper or lower first deciduous molar tooth or lower first deciduous molar tooth, and wherein a mesiodistal radius of curvature of the base is in the range of 3-11 mm.

6. The method of claim 4, wherein the deciduous tooth is a lower second deciduous molar tooth, and wherein a mesiodistal radius of curvature of the base is in the range of 8-11 mm.

* * * * *